United States Patent [19]

Barrau et al.

[11] Patent Number: 4,816,232

[45] Date of Patent: Mar. 28, 1989

[54] APPARATUS FOR CLEANING AND STERILIZING CONTACT LENSES

[76] Inventors: Bernard Barrau, 10 Rue Delcasse, 09000 Foix; Francis Bielsa, Goutte Madere, 09000 Pailhes, both of France

[21] Appl. No.: 912,763

[22] Filed: Sep. 29, 1986

[30] Foreign Application Priority Data

Sep. 30, 1985 [FR] France .................................. 85 14571

[51] Int. Cl.⁴ ............................................... A61L 2/18
[52] U.S. Cl. ......................................... 422/301; 74/72; 134/56 R; 134/79
[58] Field of Search ............... 422/116, 292, 297, 300, 422/301; 134/56 R, 78, 79, 80; 74/71, 72, 422, 30, 89.18; 206/5.1

[56] References Cited

U.S. PATENT DOCUMENTS

| | | | |
|---|---|---|---|
| 755,634 | 3/1904 | Dietz | 74/72 |
| 2,535,110 | 12/1950 | Wishart | 134/79 |
| 2,615,455 | 10/1952 | Persson | 134/78 |
| 3,837,805 | 9/1974 | Boucher | 422/301 |
| 4,013,410 | 3/1977 | Thomas et al. | 422/30 |
| 4,022,429 | 5/1977 | Yonekura | 74/422 |
| 4,143,116 | 3/1979 | Meltzer | 422/116 |
| 4,381,285 | 4/1983 | Wittenberg | 422/300 |
| 4,432,692 | 2/1984 | Breneman | 414/749 |

FOREIGN PATENT DOCUMENTS

| | | | |
|---|---|---|---|
| 469469 | 8/1975 | U.S.S.R. | 134/242 |
| 1429986 | 3/1976 | United Kingdom | 134/78 |
| 3674273 | 3/1976 | United Kingdom | 134/78 |

*Primary Examiner*—Barry S. Richman
*Assistant Examiner*—Timothy M. McMahon
*Attorney, Agent, or Firm*—Young & Thompson

[57] ABSTRACT

The present invention relates to an apparatus for cleaning and sterilizing objects for example contact lenses, of the type of those comprising two containers, one for the sterilizing solution and the other for the neutralizing solution and a timer which actuates at the end of a predetermined interval a mechanical movement for transferring the contact lenses already sterilized in the first container during the predetermined interval, the apparatus being characterized by a movable device which carries and maintains the case for the lenses during their transfer from the sterilizing solution to the neutralizing solution.

1 Claim, 5 Drawing Sheets

APPARATUS FOR CLEANING AND STERILIZING CONTACT LENSES

The present invention concerns an apparatus for cleaning and sterilizing objects, for example contact lenses. It concerns more particularly an apparatus which, starting from a predetermined soaking interval of the said lenses in a sterilizing solution, transfers them into a neutralizing solution so as to reduce the residue from the first solution and permit them to be conveniently stored in anticipation of their use.

For daily chemical sterilization by an oxidizing system, the contact lenses are placed for a predetermined interval in a sterilizing solution (for example hydrogen peroxide). At the end of this interval the sterilization is complete, and they are transferred into a neutralizing solution: they are allowed to soak for at least the time recommended by the manufacturer of the products. After this time, the wearer may put on his lenses which are thus antiseptically cleaned and preserved in a hydrated state.

The interval during which the contact lenses remain in the sterilizing solution must be sufficient for complete sterilization to take place. On the other hand, unnecessary extension of the said interval helps to cause an ever-growing number of active molecules to cling on the surface and within the said lenses. This necessitates a longer interval for neutralizing these molecules. Once a week, so as to remove protein deposits on the lenses, they are soaked for a predetermined time in a solution containing deproteinizing agents. Next, either they are transferred to a rinsing solution, or the previously described daily cleaning cycle is resumed.

U.S. Pat. No. 4,381,285 teaches ejecting the case for the lenses toward the neutralization container once its sterilization interval is completed in the sterilization container. Such an apparatus prevents having to carry out manually the operation of transferring the contact lenses from the sterilizing solution to the neutralizing solution at the end of a predetermined interval. Nevertheless, the apparatus which has just been mentioned has the following disadvantages:

the lenses are subjected to a mechanical shock at the time of their ejection, a portion of the sterilizing solution is transferred, at the same time as the lenses, to the neutralizing solution, because of the manner in which the said transfer is effected, the two solutions, sterilizing and neutralizing, are caused to spatter at the time of the said transfer.

So as to overcome these disadvantages, the present invention proposes an apparatus for effecting such a transfer without violent movement, while giving the case time to drain.

To this end, the present invention is characterized essentially by a movable means which carries and maintains the case of the contact lenses during their transfer from the sterilizing solution to the neutralizing solution.

The present invention will be better understood from a reading of the following detailed description illustrated by the drawings in which.

Figure 1:
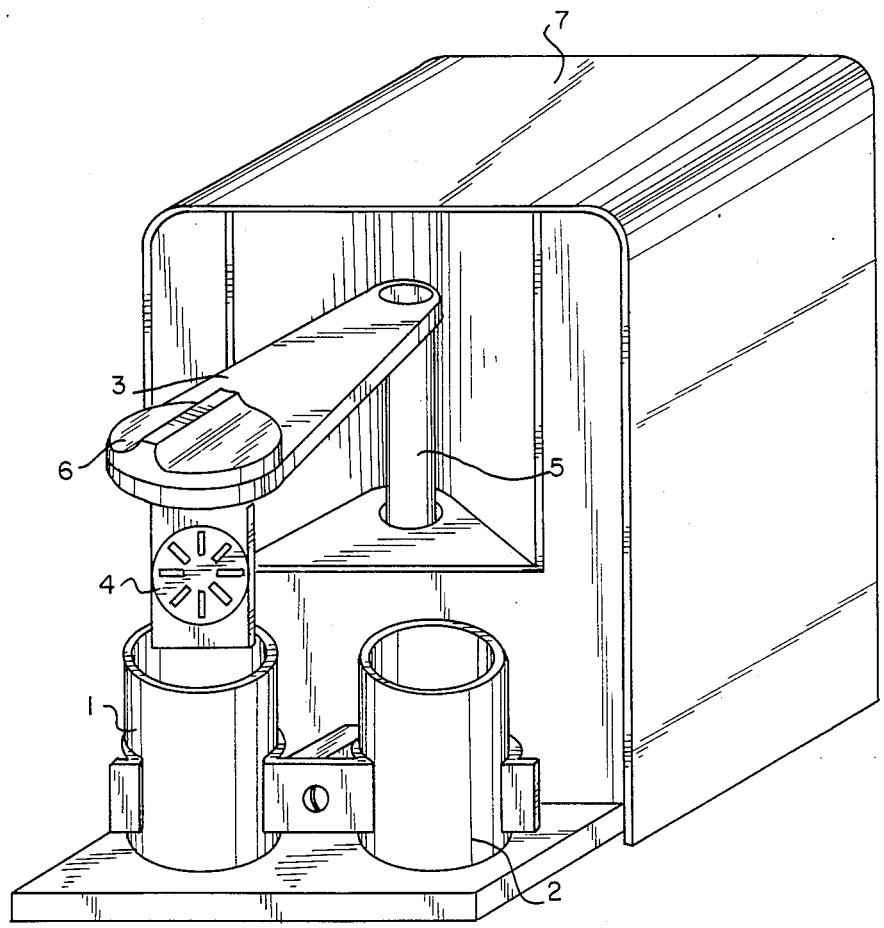
FIG. 1 is a perspective view of the apparatus

According to the present invention, the sterilizing apparatus comprises two containers (1) and (2) intended to contain respectively the sterilizing solution and the neutralizing solution, an arm (3) carrying the case (4) containing the contact lenses.

The said arm is fixed to a vertical slide (5) displaceable along a vertical axis and rotatable about the same axis, and consequently the portion of the arm which carries the case (4) effects either a vertical movement parallel to the said axis or a rotary movement along a circular arc of which the center is disposed on the said axis or a combination of these two movements. Preferably, the arm (3) is fixed to the upper end of the slide. The arm (3) carries a cover (6) adapted to the containers (1) and (2). The case (4) is removably attached to the said cover such that it will be contained in the container once this latter is covered. The said arm is preferably disposed horizontally. A hole near its free end holds the cover (6) in suspension.

At the beginning of the cycle, the arm (3) is in its downward position, and the case (4) is housed in the container (1) containing the sterilizing solution. At the end of a predetermined interval set by a horological mechanism or any other means for keeping time, a motor means associated with this horological mechanism drives the arm in an ascending vertical movement, followed by a rotary movement at the end of which the case (4) will be above the container (2) and finally in a descending vertical movement at the end of which the case (4) is immersed in the neutralizing solution contained in the container (2). The motor means and the horological mechanism are mounted in a casing (7). A sealing joint is disposed between the slide (5) and the timekeeper casing (7) such that cleaning of the exterior of the apparatus with water does not expose the motor means and the horological mechanism to humidity. The two containers (1) and (2) may be fixed on the apparatus or may be removable (detachable).

Figure 2:
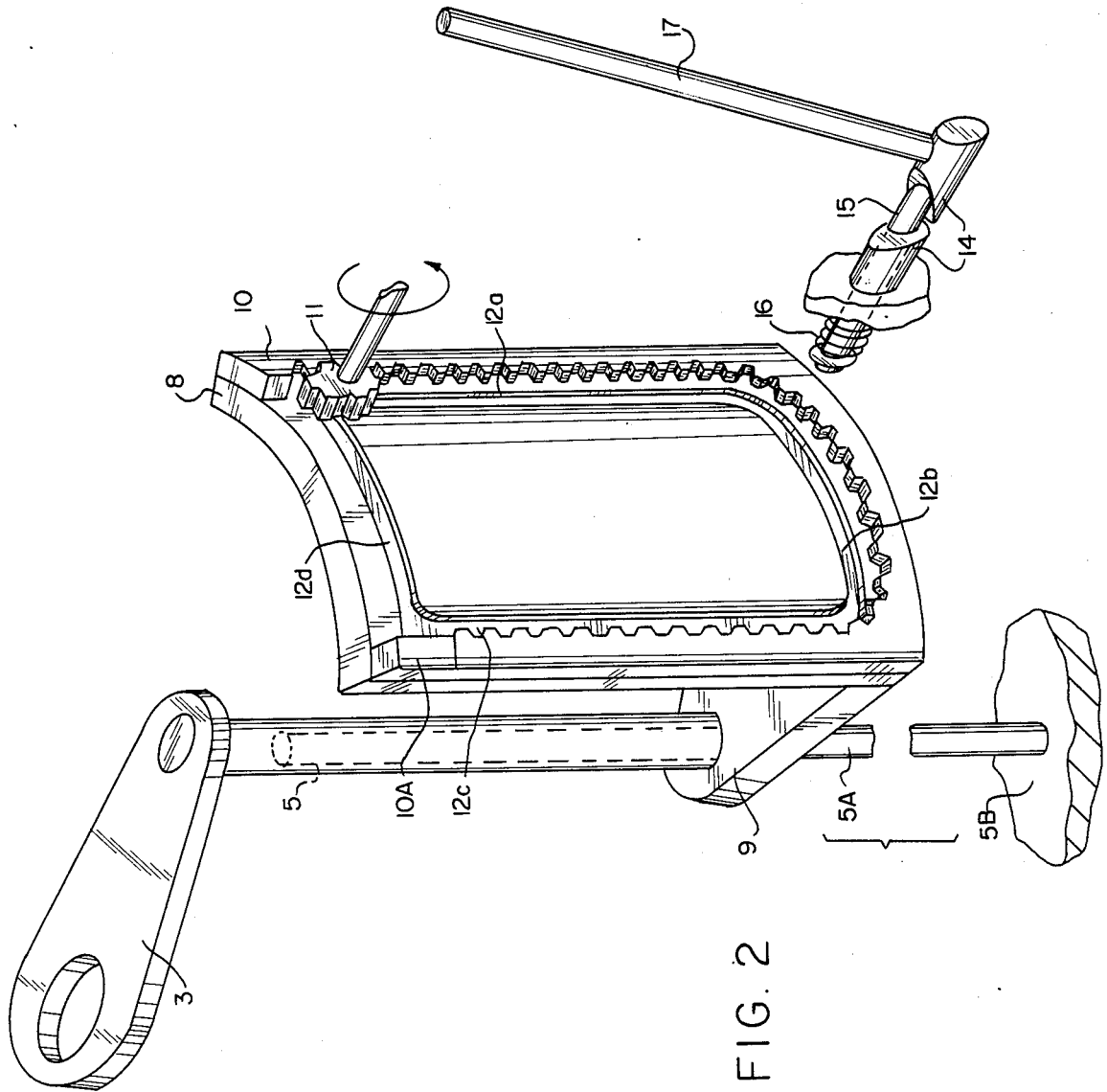
FIG. 2 is a view which shows the mechanism producing the movement for effecting the said transfer.
Figure 3B:
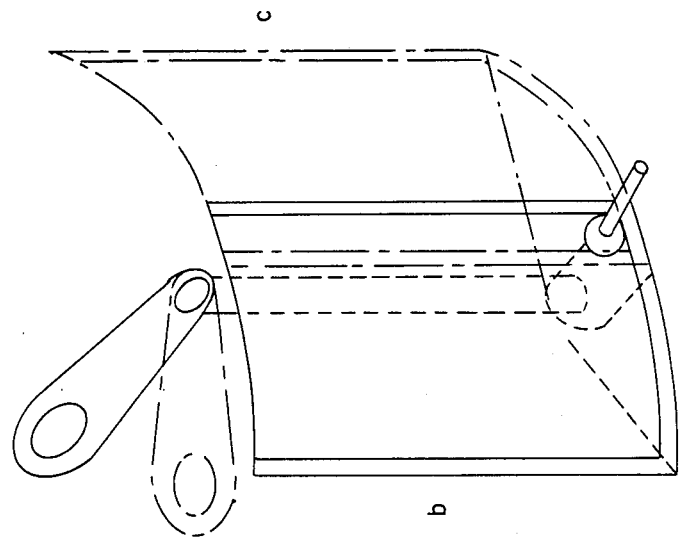
FIGS. 3A, 3B, 3C and 3D show the successive movements of the means for maintaining and carrying the contact lenses.
Figure 3A:
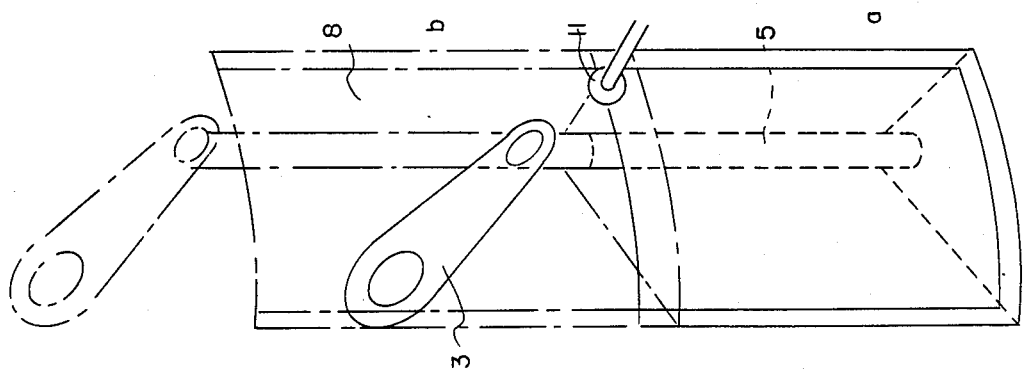
Figure 3D:
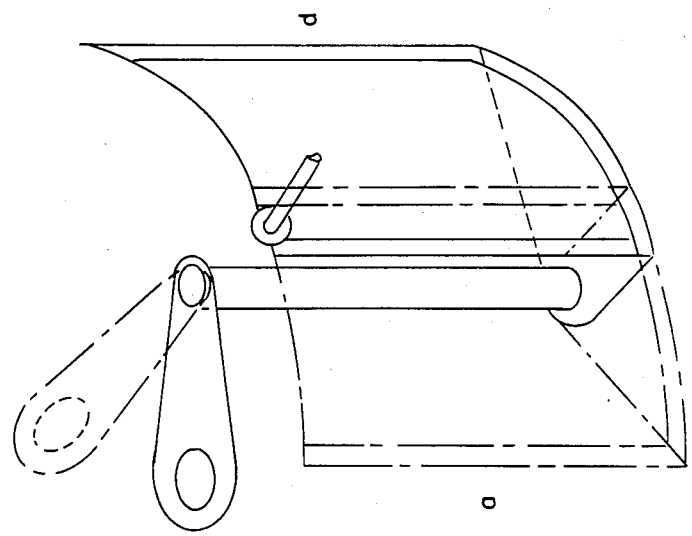
Figure 3C:
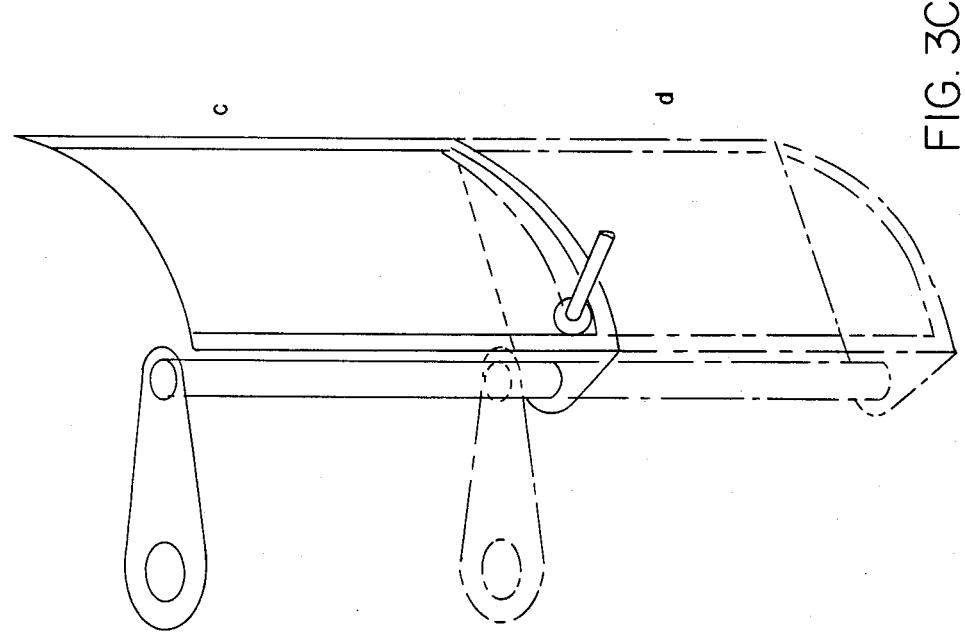
Figure 4A:
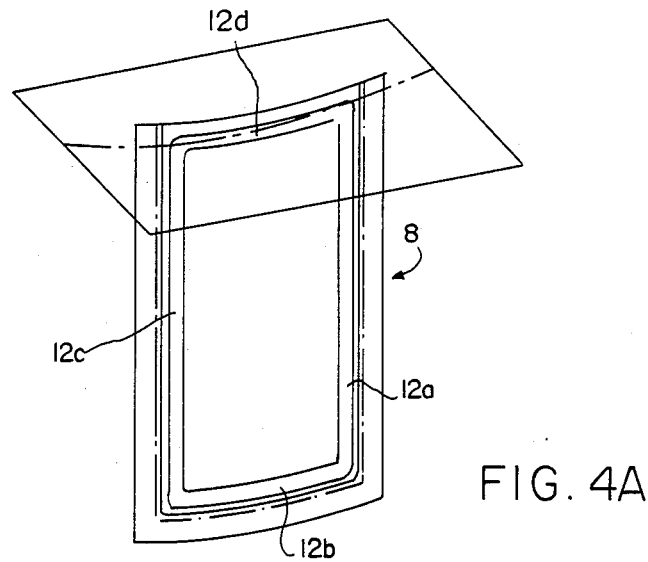
FIG. 4A and FIG. 4B show how the guiding, which assures contact between the motor mechanism and the movable portion of the apparatus, is effected.
Figure 4B:
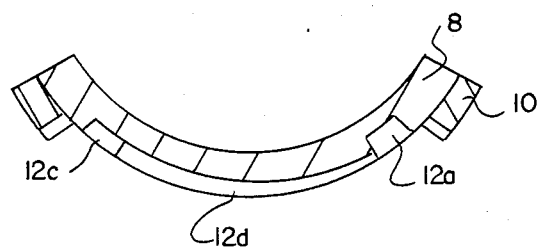

FIG. 2 shows by way of example an embodiment of the mechanism which imparts a succession of movements forming a cycle: an ascending vertical movement, a movement along a horizontal plane and finally a descending vertical movement. This movement is obtained by the following mechanism:

A plate (8) is curved around the axis of the slide (5) and fixed to this latter via a support (9). The slide (5) is mounted on a column (5a) fixed to a base (5b). Movement of the plate (8) parallel to or about the axis of the slide: "the axis of the column (5a)" communicates with the arm (3) respectively either in the form of a simultaneous movement of translation or in the form of an angular movement of the same value as that of the plate. A reinforcement (10) is provided on the outer surface of the plate. A rotary mechanism (11) cooperates by friction or by gearing with the said reinforcement so as to drive the plate (8) according to the orientation give to the reinforcement. So as to effect the three desired movements—ascending vertical movement, movement in a horizontal plane and descending vertical movement—the reinforcement provided on the surface of the plate is composed of a descending vertical portion followed at its lower level by a horizontal portion, then by a second ascending vertical portion.

According to a preferred form of a invention, the reinforcement (10) is a rack and the rotary mechanism (11) is a toothed pinion. A groove (12) is made parallel to the rack on the same surface of the plate, for housing a guide finger (13) (FIG. 5), which ensures contact between the pinion (11) and the rack (8). This groove is composed of four parts: the part (12a) parallel to the first vertical portion of the rack for assuring the ascending vertical movement, the part (12b) parallel to the horizontal portion of the rack for assuring movement along a horizontal plane, the part (12c) parallel to the second vertical portion of the rack for assuring the descending vertical movement and the part (12d) for assuring passage of the pinion finger (13) from the final position of the cycle to the initial position of this latter for permitting commencement of a new cycle.

The depth of the portion (12d) of the groove has the same value as that of the portion (12c) at the level of their coincidence, whereas it has a value less than that of the part (12a) at the level of their coincidence, as is shown in FIG. (4B), which is a sectional view of FIG. (4A) at the level of the part (12d), which permits a continuous passage from (12c) to (12d), but once the finger (13) is engaged in the part (12a) it can no longer return to (12d), which assures good contact between the rack and the pinion at the commencement of the cycle.

FIGS. (3A), (3B), (3C) and (3D) show the successive steps corresponding to the different movements of the plate (8) and consequently of the arm (3). At the beginning of the cycle the plate is at position (a) as shown in FIG. (3A), the lens case is in the first container, immersed in the sterilizing solution. At the end of a predetermined interval, any timer (not shown) releases a mechanism which drives the pinion (11) in rotation and consequently the plate effects an ascending vertical movement to assume position (b). At this latter position (b) the lens case is outside of the container (1) but remains facing this latter.

The pinion (11) continues to turn, driving the plate to the position c, as shown in FIG. (3B). In this position, the arm that carries the lens case is above the container (2). FIG. (3C) shows position (d) in which the case with the lenses are immersed in the neutralizing solution contained in the container (2). The lenses remain in this latter, in anticipation of their use.

The last part (10a) of the rack (10) corresponding to the end of the cycle is not toothed. This permits the pinion (11) to turn freely so as to disconnect the drive spring in the case of a mechanical driving. In the case where an electric motor is used, this latter will be permitted to function for a predetermined interval greater than that necessary for the transfer of the case from one container to the other. The said interval, during which the motor is permitted to function, takes into consideration the wearing out of the electric batteries and consequently the lengthening of the transfer interval. So as to commence another cycle like that which has just been described, the plate is reset manually to the position (a), by acting on the arm.

For safety, and to be sure that the timer and the actuating mechanism for the pinion are operating, changing of the position of the plate from position (c) to position (d) will be permitted only if the said operation is effected.

The purpose of conditioning the change in position on the operation of the timer and the actuating mechanism of the pinion is to assure transfer of the lenses from the sterilizing solution to the neutralizing solution at the end of a predetermined interval. So as to assure, according to the invention, the application of such a condition, two embodiments are given by way of example. One of these embodiments is shown in FIG. 2; it is constituted by a cam (14) formed of two parts, one fixed part through which passes a shaft (15) and the second part is integral therewith.

A spring (16) urges the shaft (15) toward the plate (8). Once the plate surrenders position for effecting its movements, the said shaft advances and passes beyond the level of the plate.

In position (d) of the plate, the said shaft passes beyond the level of the plate from the left and prevents it from resuming its initial position.

A lever (17) is fixed to the shaft (15), and actuation of this lever causes the said shaft to turn and consequently removes it from the plate. Such an actuation of the lever may be effected by the same action that operates the timer, for example with a mechanical motion to be made for winding the timer.

Figure 5A:
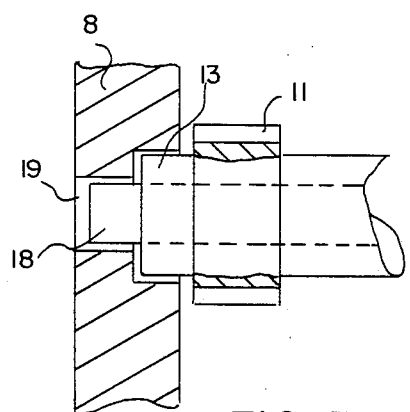
FIG. 5A and FIG. 5B show the arrangement of the motor mechanism for assuring contact with the movable portion and also for blocking it at the end of its run.
Figure 5B:
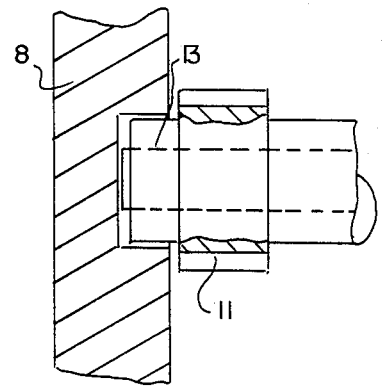

Locking of the plate at the end of the cycle can also be effected as shown in FIG. 5. A retractable finger (18) coaxial with the pinion (11) lodges, at the end of the course, in a hollow (19) made in the plate (8). This finger is retracted, in a known manner, either after the clock has been wound or with the aid of any mechanism for freeing the plate.

The operation of the apparatus is as follows:

The contact lenses are placed in their case,

After having turned on the timer, the case carried by the arm is positioned in the first container containing the sterilizing solution, At the end of a predetermined interval, the arm effects a series of three movements: an ascending vertical movement, a horizontal movement followed by a descending vertical movement at the end of which the case for the lenses will be immersed in the second container.

In this latter position, the plate will be blocked and return to the initial position is authorized in this case only when the operation of the timer is effected.

It is evident that the succession of movements of the arm described above could be effected with other purely mechanical, hydraulic, electromechanical or other equivalent means, without departing from the scope of the present patent.

We claim:

1. Apparatus for sterilizing contact lenses, comprising two containers, one for sterilizing solution and the other for neutralizing solution and a timer which releases, at the end of a predetermined interval, a mechanical movement means for transferring the contact lenses already sterilized in the first container during said interval to said other container, said mechanical movement means comprising a movable means which carries and maintains a case for the lenses during their transfer from said one container to said other container, said movable means comprising a vertical plate having a cylindrical surface and provided with a rack having two straight vertical legs and a part-circular horizontal leg coaxial with said cylindrical surface, said rack engaging a driven pinion, said plate being connected by a support to a tubular slide sliding and rotating on a vertical cylindrical column the axis of which is the same as that of the cylindrical surface of the plate and of the part-circular rack leg, said slide carrying an arm which carries near its end a case for the contact lenses, there being a groove parallel to the rack, in which is housed a guide finger connected to said pinion for assuring its contact with the rack, said groove being parallel to the rack over all its length from a first position of the pinion, relative to said rack, to a second position of the pinion, said groove extending from this second position, to said first position, thus forming an endless circuit for permitting the pinion to return to said first position with respect to said rack while rotating at all times in the same direction, a portion of the groove connecting said second position of the pinion to its said first position having a depth less than that of the groove at said first position of the pinion, thereby preventing reverse movement of said finger about said endless circuit when said pinion is in said first position.

* * * * *